United States Patent [19]
Cooper

[11] Patent Number: 5,824,020
[45] Date of Patent: Oct. 20, 1998

[54] RATE-RESPONSIVE PACEMAKER WITH RAPID MINUTE VOLUME DETERMINATION

[75] Inventor: Daniel Cooper, Hauguenau, France

[73] Assignee: Pacesetter, Inc., Sylmar, Calif.

[21] Appl. No.: 850,557

[22] Filed: May 2, 1997

[51] Int. Cl.$^6$ .............................. A61N 1/365; A61N 1/362
[52] U.S. Cl. ................................................ 607/17; 607/17
[58] Field of Search ........................................ 607/17–19

[56] References Cited

U.S. PATENT DOCUMENTS

| | | |
|---|---|---|
| 4,873,980 | 10/1989 | Schaldach . |
| 4,901,725 | 2/1990 | Nappholz et al. . |
| 5,063,927 | 11/1991 | Webb et al. ............................... 607/19 |
| 5,318,597 | 6/1994 | Hauck et al. .............................. 607/20 |
| 5,441,523 | 8/1995 | Nappholz . |
| 5,487,753 | 1/1996 | MacCarter et al. . |
| 5,562,712 | 10/1996 | Steinhaus et al. . |
| 5,626,622 | 5/1997 | Cooper . |
| 5,645,575 | 7/1997 | Stangl et al. . |
| 5,713,938 | 2/1998 | Chiang et al. . |

*Primary Examiner*—William E. Kamm
*Assistant Examiner*—Carl H. Layno
*Attorney, Agent, or Firm*—Gottlieb, Rackman & Reisman, P.C.

[57] ABSTRACT

A rate responsive pacemaker with improved response to exercise onset includes a detector for detecting a metabolic parameter indicative of the patient's metabolic demand. The metabolic demand parameter derived therefrom is analyzed either using a heart rate sensitive zero crossing detector or a derivative calculator and used to generate an optimized pacing rate.

11 Claims, 12 Drawing Sheets

COMPUTATION INTERVAL = ABOUT 1.5S rr = RESPIRATION RATE, BREATHS PER MINUTE
tv = TIDAL VOLUME dmv1 = UNFILTERED DELTA MINUTE VENTILATION
baseline = mv AT MINIMUM HEART RATE s2 = SUM OF ti VALUES BETWEEN ZERO CROSSINGS
s3 = PREVIOUS VALUE OF s2 t2 = TIME BETWEEN ZERO CROSSINGS
t3 = PREVIOUS VALUE OF t2 zc1 = ZERO CROSSING COUNT
zc2 = PREVIOUS VALUE OF zc1

RATE-RESPONSIVE PACEMAKER WITH RAPID MINUTE VOLUME DETERMINATION

RELATED APPLICATIONS

The subject matter of this application is related to applications RTE-RESPONSIVE PACEMAKER WITH NOISE-REJECTING MINUTE VOLUME DETERMINATION, Ser. No. 08/848,968 filed on May 2, 1997 RATE-RESPONSIVE PACEMAKER WITH MINUTE VOLUME DETERMINATION AND EMI PROTECTION, Ser. No. 08/850,529 filed on May 2, 1997, RATE-RESPONSIVE PACEMAKER WITH EXERCISE RECOVERY USING MINUTE VOLUME DETERMINATION, Ser. No. 08/850,692 filed on May 2, 1997.

BACKGROUND OF THE INVENTION

1. Field of the Invention

This invention relates to rate-responsive pacemakers and, more particularly, to pacemakers that employ a minute volume metabolic demand sensor as a metabolic rate indicator, said sensor having a fast response time to thereby insure that the pacemaker reacts quickly and accurately to changes in the level of activity of a patient such as, for example, onset of exercise.

2. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include the QT interval, respiration rate, venous oxygen saturation, stroke volume, venous blood temperature, and minute volume or ventilation, among others. (The terms minute ventilation and minute volume are used interchangeably). In addition, the use of mechanical and electrical sensors which detect patient motion have also been explored in such attempts at achieving improved rate-responsiveness.

Of the various parameters available, it has been found that pacemakers using minute volume as a parameter for controlling pacing rate are particularly advantageous. However, a problem with these types of pacers has been that the means of converting this parameter into an actual metabolic indicated parameter which may be used to determine the optimal interval between pacing pulses was somewhat slow.

A further problem is that, in general, even though metabolically-related parameters used for controlling rate-responsive pacemakers, especially the tidal volume component of minute ventilation react fairly rapidly in reflecting changes in the patient's physical activity, the pacemakers' circuitry does not react with the same speed or time constant. This can result in the patient having a hemodynamic deficiency due to the lag time involved between the start of an increased level of exercise and the reaction thereto by the pacemaker.

A further problem with prior art pacemakers is that they incorporate a long term filter in the minute volume determination to determine a minute volume baseline. The filter approximates the median minute volume ventilation but its output varies during extended exercise. Therefore, extended exercise may result in an initial value which is too high or a final value which is too low.

OBJECTIVES AND SUMMARY OF THE INVENTION

In view of the above mentioned disadvantages of the prior art, it is an objective of the present invention to provide a pacemaker which dynamically responds to the instantaneous physical level of activity of a patient and adjusts its pulse rate accordingly.

A further objective is to provide a metabolic rate responsive pacemaker which is capable of generating a metabolic indicated rate parameter relatively rapidly to thereby eliminate a lag between onset of physical activity and the corresponding response or adjustment by the pacemaker.

Another objective is to provide a pacemaker which automatically tracks in the minute volume baseline and adjusts its rate response function used to map the minute volume into the metabolic indicated rate accordingly.

Other objectives and advantages of the invention shall become apparent from the following description. Briefly, a pacemaker constructed in accordance with this invention includes sensing means for sensing a metabolic demand parameter of the patient indicative of his or her instantaneous physical activity. Preferably, the metabolic demand parameter is minute volume which can be determined, for example, from impedance measurements. Minute volume has been found to be an accurate representation of the physical activity and the corresponding blood flow and oxygen demand of a patient. This parameter is converted into a corresponding metabolic indicated rate (MIR), which rate may be used to define the interval between the pacer pulses. The mapping of minute volume to metabolic indicated rate (MIR), preferably, uses a preselected curve which may be, for example, an exponential curve, or other monotonic curves. In one embodiment of the invention, the minute volume is determined using a breath by breath computation. In another embodiment the minute volume is determined by taking a derivative of the tidal volume. The resulting rate is then used to calculate a optimal paced pulse interval.

It should be understood that rate responsive systems making use of the minute volume as a parameter first calculate a long term average for the minute volume of a patient and then determine the difference between this long term average and an instantaneous minute volume obtained as described below. The resulting differential parameter is referred to as "the minute volume" for the sake of brevity. However, in the drawings, the parameter is identified as dmv or delta MV to indicate that, in fact, this parameter corresponds to the variation of the instantaneous minute volume from a long term average value.

DETAILED DESCRIPTION OF THE INVENTION

Figure 1:
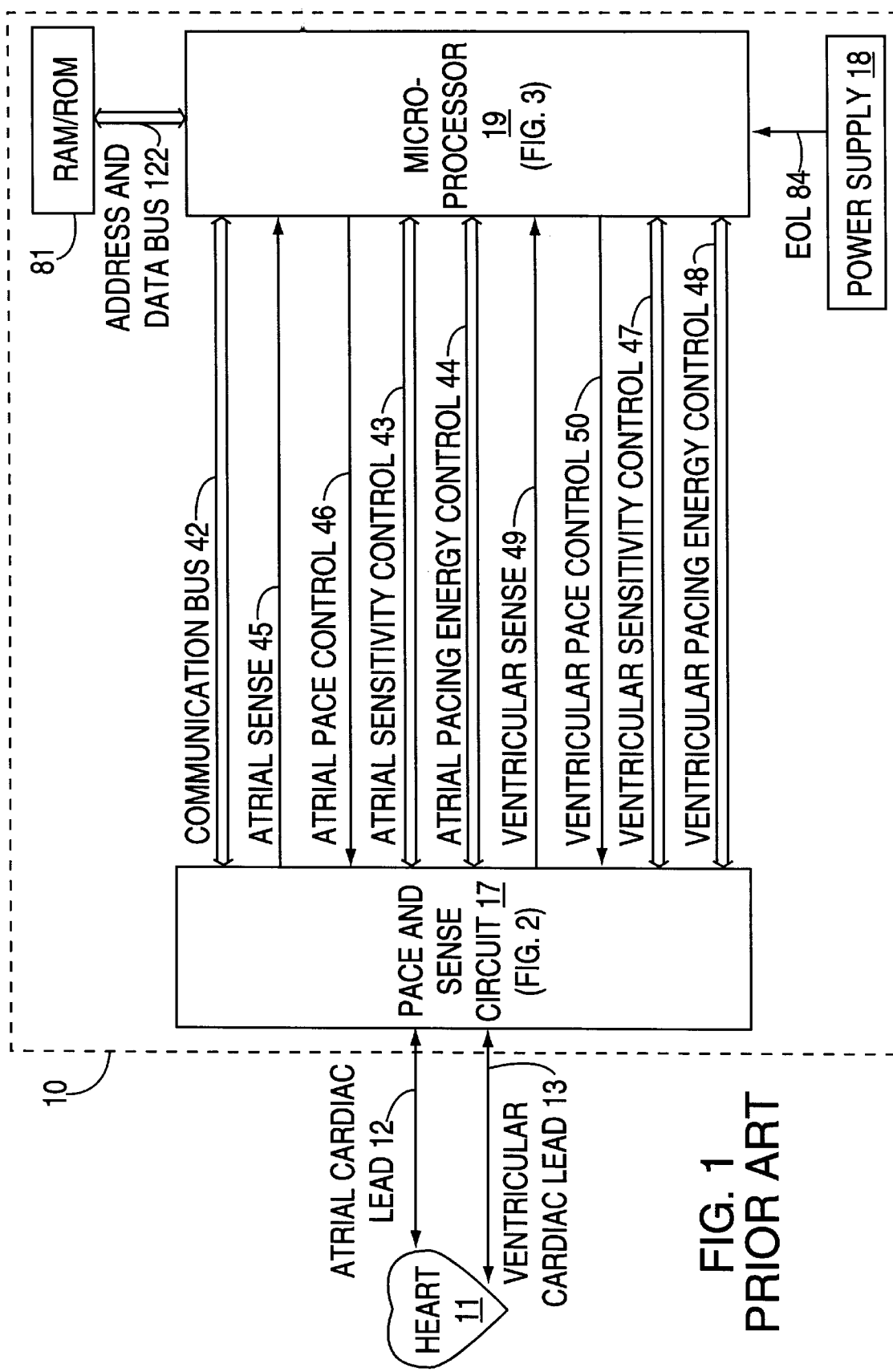
FIG. 1 shows a block diagram of a pacemaker constructed in accordance with this invention.

Details of a pacemaker in accordance with the present invention are shown in FIGS. 1–6. FIG. 1 shows a block diagram of the pacemaker. The pacemaker 10 is designed to be implanted in a patient and is connected by leads 12 and 13 to a patient's heart 11 for sensing and pacing the heart 11 as described for example in U.S. Pat. No. 5,441,523 by T. Nappholz, entitled FORCED ATRIOVENTRICULAR SYNCHRONY CHAMBER PACEMAKER, and incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 81 by an address and data bus 122. A low power signal line 84 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
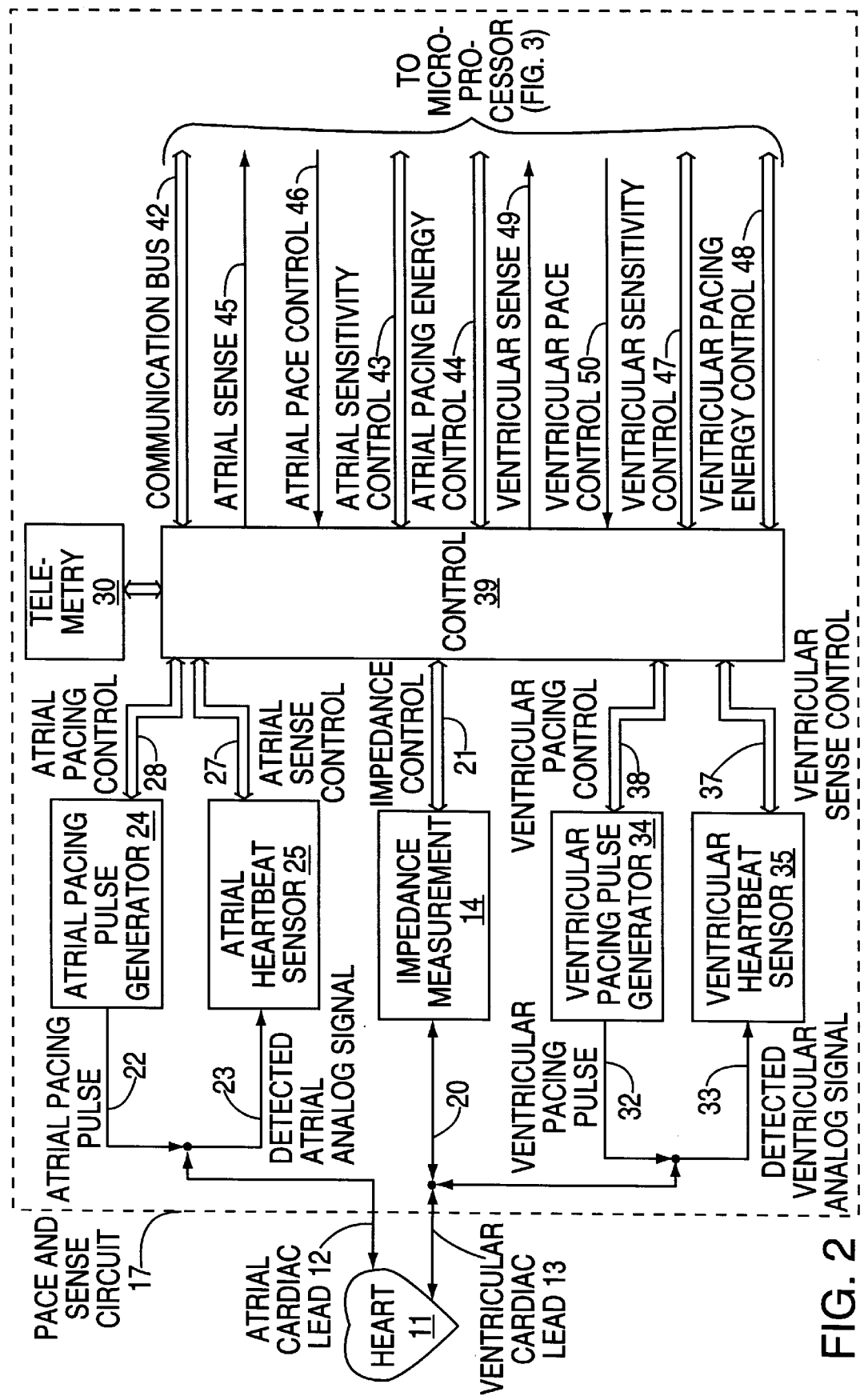
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that take place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current, as discussed in more detail below. These current and voltage signals define an impedance characteristic of the patient's metabolic demand, and more particularly, of the instantaneous minute volume. This instantaneous minute volume is then filtered and further modified by subtracting from it a long term average value, as discussed below. The resulting parameter is the minute volume parameter.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the Model 9600 Network Programmer manufactured by Telectronics of Englewood, Colo., U.S.A.

Figure 3:
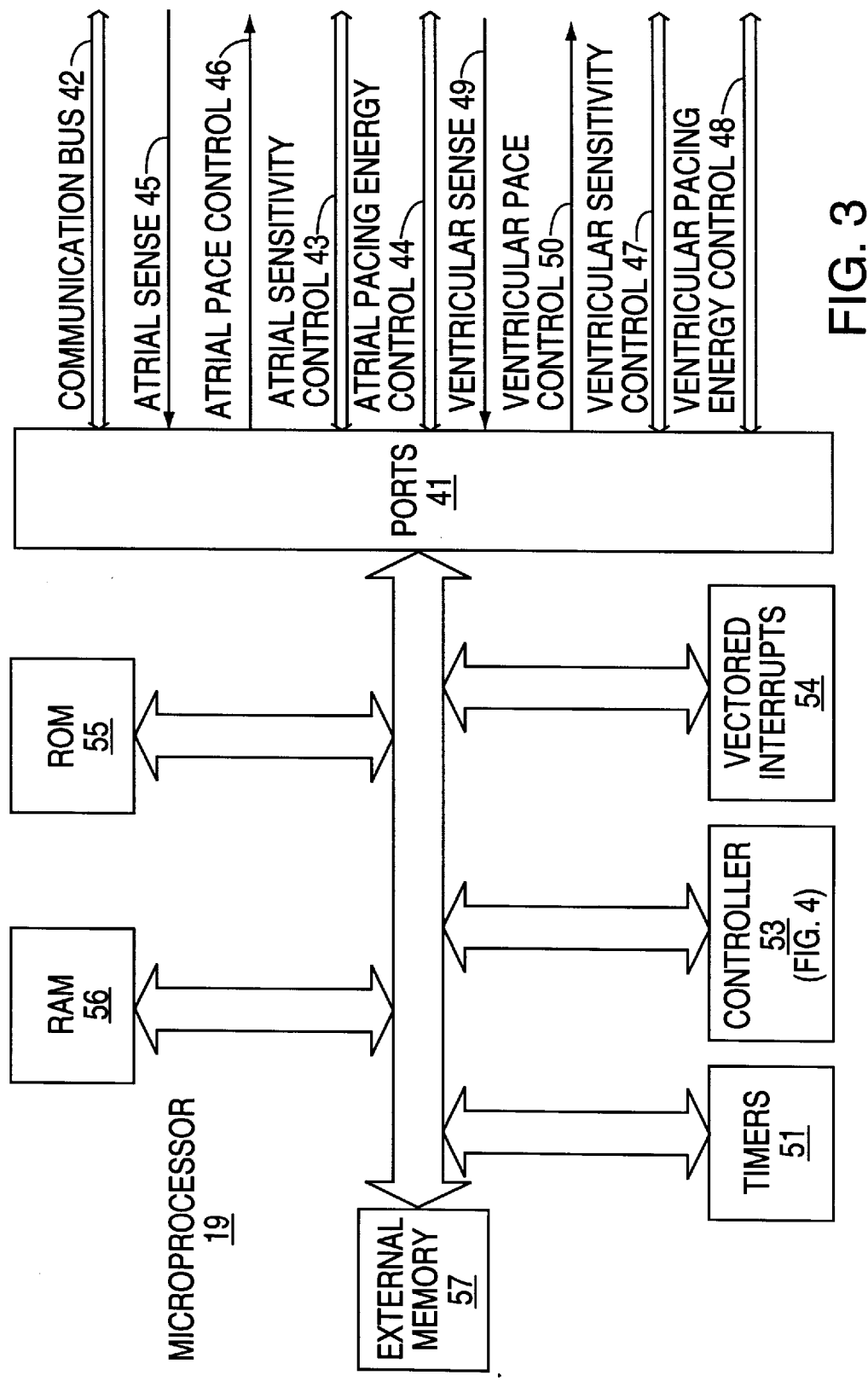
FIG. 3 shows a block diagram of a microprocessor for the pacemaker of FIG. 2.

FIG. 3 shows the microprocessor 19 having a timer circuit 51 for generating several timing signals on its output ports, a controller 53, a vectored interrupts circuit 54, a ROM 55, a RAM 56, an external memory 57 and an interface port 41. Signals between these elements are exchanged via an internal communications bus 40. Timer circuits 51 generate various timing signals. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data concerning the functioning of the pulse generator 10 and the electrogram provided by the ventricular cardiac lead 13. The timer circuit 51, and its associated control software, implements some timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives status and/or control inputs from the pace and sense circuit 17, including the sense signals on the sense lines 45 and 49 previously described. Using controller 53, it performs various operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricular pacing is adjusted by controller 53 as set forth below.

The pacemaker 10 of the present invention will function properly using any metabolic indicator rate system, so long as that system is able to reliably relate the sensed parameter to an appropriate matching of metabolic demand with the paced rate. However, the preferred embodiment of the invention employs the impedance measurement circuit 14, shown in FIG. 5, which measures the cardiac impedance to determine the respiratory minute volume as described generally in U.S. Pat. No. 4,901,725 to T. A. Nappholz, et al., issued Feb. 20, 1990 for "Minute Volume Rate-Responsive Pacemaker," incorporated herein by reference.

Figure 4:
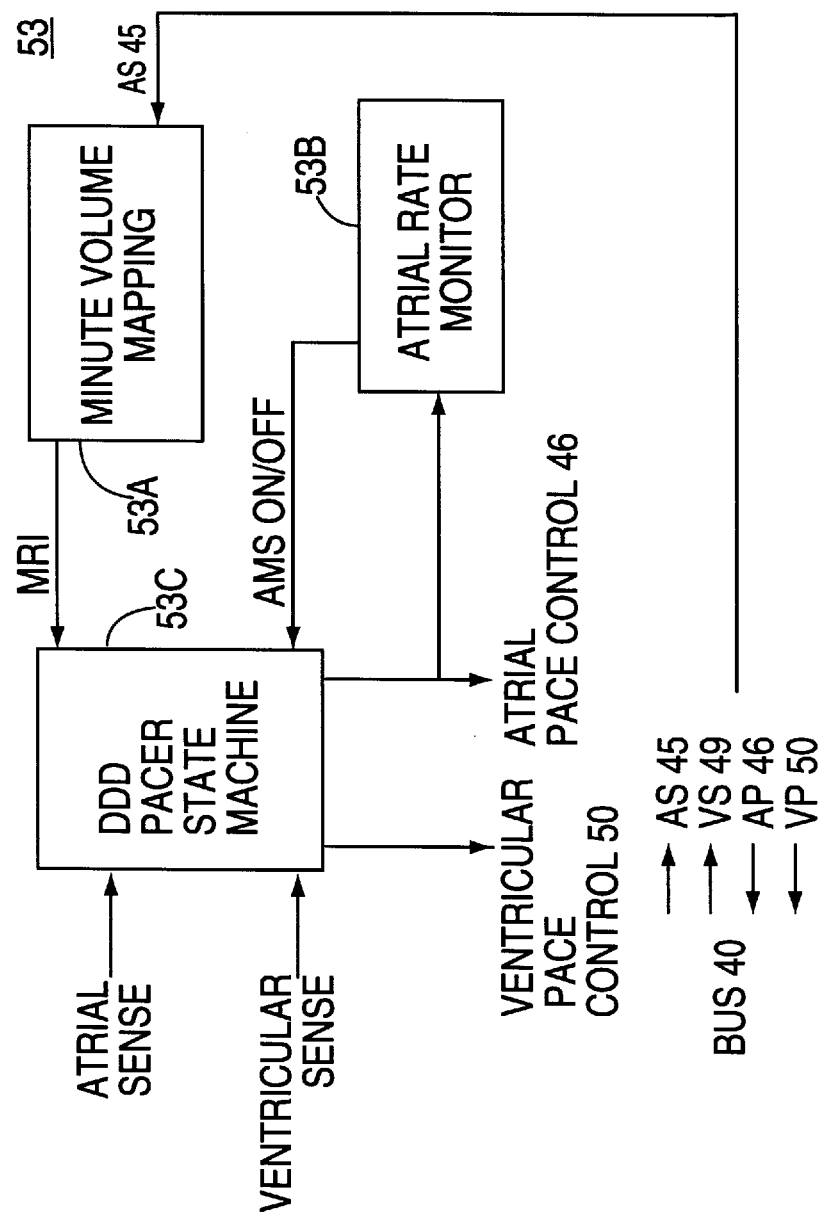
FIG. 4 shows details of the controller for the microprocessor of FIG. 3.

FIG. 4 shows the block diagram of the controller 53 of FIG. 3. The controller 53 includes a pacer 53C, which is preferably a state machine, a minute volume processor 53A and an atrial rate monitor 53B. The minute volume processor 53A uses the data supplied via the internal bus 40 and the communication bus 42 from the impedance measurement block 14 to relate the minute volume indicated by the impedance measurement to the Metabolic Rate Interval (MRI). This interval is then used by the pacer 53C to determine the length of each interval in the timing cycle. While the pacemaker 10 is preferably operating in a DDD mode, it should be understood that it can operate in other modes as well. The atrial rate monitor 53B generates an Automatic Mode Switching (AMS) signal upon detection of a nonphysiological atrial rate and rhythm. This AMS signal automatically switches the pacemaker 10 to a non-atrial-tracking mode under certain conditions. When a physiological atrial rate resumes, the AMS signal is deactivated and the pacemaker returns to an atrial tracking mode.

Figure 5:
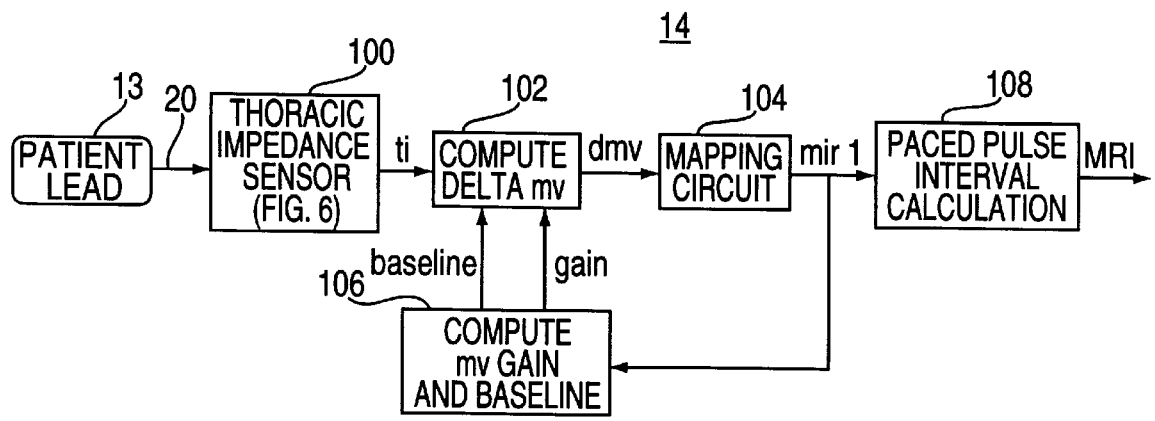
FIG. 5 shows details of the minute volume processor for the controller of FIG. 4.
Figure 7:
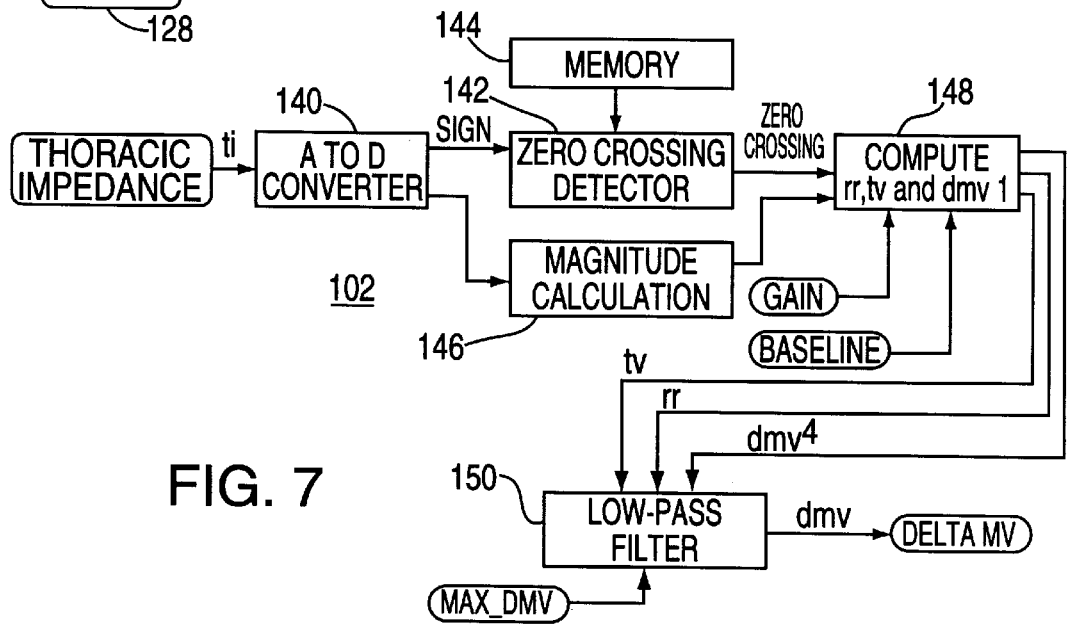
FIG. 7 shows details of the circuitry used to convert the thoracic impedance into a corresponding differential minute volume.

Referring now to FIG. 5, impedance measurement circuit 14 includes a thoracic impedance sensor 100 which is coupled by connection 20 to one of the patient's leads, such as lead 13. The sensor 100 generates a time-dependent signal ti indicative of the sensed thoracic impedance of the patient. The signal is fed to a delta minute ventilation (dmv) generator 102 which converts this ti signal into a corresponding dmv signal as indicated in FIG. 7 and discussed in more detail below. The signal dmv is fed to a circuit 104 which uses a conformal mapping (discussed in more detail below) to generate a corresponding metabolic indicated rate MIR1.

Signal MIR1 is fed to a paced pulse interval calculation circuit 108. The interval MRI calculated by circuit 108 is used by the state machine 53 (FIG. 4) to calculate the pacing intervals as discussed above.

Signal MIR1 is also provided to circuit 106 for computing an mv gain and a baseline parameter as discussed below.

Figure 6:
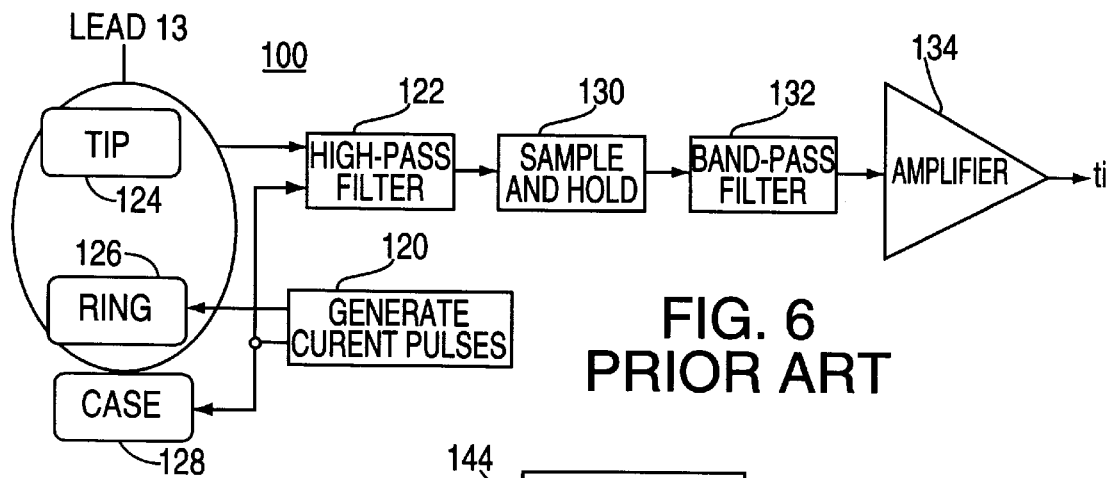
FIG. 6 shows a block diagram for the circuit used to determine thoracic impedance.

Referring now to FIG. 6, a known thoracic impedance sensor 100 includes a current generator 120 and a high pass filter 122 coupled to one of the patient leads, such as lead 13.

(It should be clear that other leads may be used as well for determining the mv parameter as described, for example, in U.S. Pat. No. 5,562,712). The lead 13 includes a tip electrode 124 and a ring electrode 126. As known in the art, at predetermined times, the current generator 120 applies current pulses between the ring electrode 126 and pacemaker case 128, and the corresponding voltage is sensed between the tip electrode 124 and case 128. Typically, each current pulse has a pulse width of about 7.5 μsec, at repetition rate of about 18 pulses per second and an amplitude of about 1 mA. This pulse repetition rate is chosen at well above twice the Nyquist sampling rate for the highest expected intrinsic heart beats, and is preferable so that it can be easily differentiable from noise induced by a power line at 50 or 60 Hz.

The sensed voltage, is passed through the high pass filter 122 selected to accept the 7.5 μsec pulses and exclude all noise signals. After filtering, the voltage signal is sampled by a sample and hold (S/H) circuit 130. Preferably the S/H circuit takes samples before the start of the test pulses from generator 120 (to enhance the effectiveness of the filter 122) as well as toward the end of the pulse duration.

The output of circuit 130 is passed through a band pass filter 132 which selects the signals in the range of normal respiration rate, which is typically in the range of 5–60 cycles/minute.

The output of the BPF 132 amplified by amplifier 134 to thereby generate the thoracic impedance signal ti. The amplifier raises the signal ti to a level sufficient so that it can be sensed and processed by the delta minute volume generator 102.

Referring to FIG. 7, circuit 102 includes an A/D converter 140, a zero crossing detector 142, a magnitude calculator circuit 146, calculator circuit 148 for calculating parameters rr, tv and dmv, and a low pass filter 150. Circuits 140 and 142 are preferably discrete hardware components while the remaining circuits 146, 148, 150 are implemented by a microprocessor, however are shown here as discrete circuits for the sake of clarity.

Within circuit 102, the thoracic impedance signal ti is first fed to an A/D converter 140 to generate a digital representation of the signal ti. This converter generates two outputs; a sign output indicating the polarity of the signal ti and a magnitude output indicating the amplitude of ti. This magnitude is of course the same as the absolute value of the signal ti.

The sign signal is fed to a zero crossing detector 142 which generates a zero crossing indicating output whenever it detects a sign change of signal ti. Associated with detector 142 is a memory 144 for storing the polarities of the last N samples from converter 140. N may be for example 15.

Preferably the zero crossing detector 142 is implemented so that it adapts to changes in the heart rate. This feature was found to improve the rejection of cardiac stroke volume artefact and other noise sources. More specifically, the zero crossing circuit detector 142 detects a zero crossing each time more than m of n successive samples have a sign opposite to the sign value which was detected at a previous zero crossing. The values m and n are adjusted according to the paced or sensed pulse rate. This insures that the zero crossing cannot be detected at the heart rate, but can be detected at lower rates. This feature is especially beneficial for pediatric patients who have a much higher respiration rate than older patients. These higher rates can be tracked more efficiently by the present zero crossing detector 142.

Figure 7A:
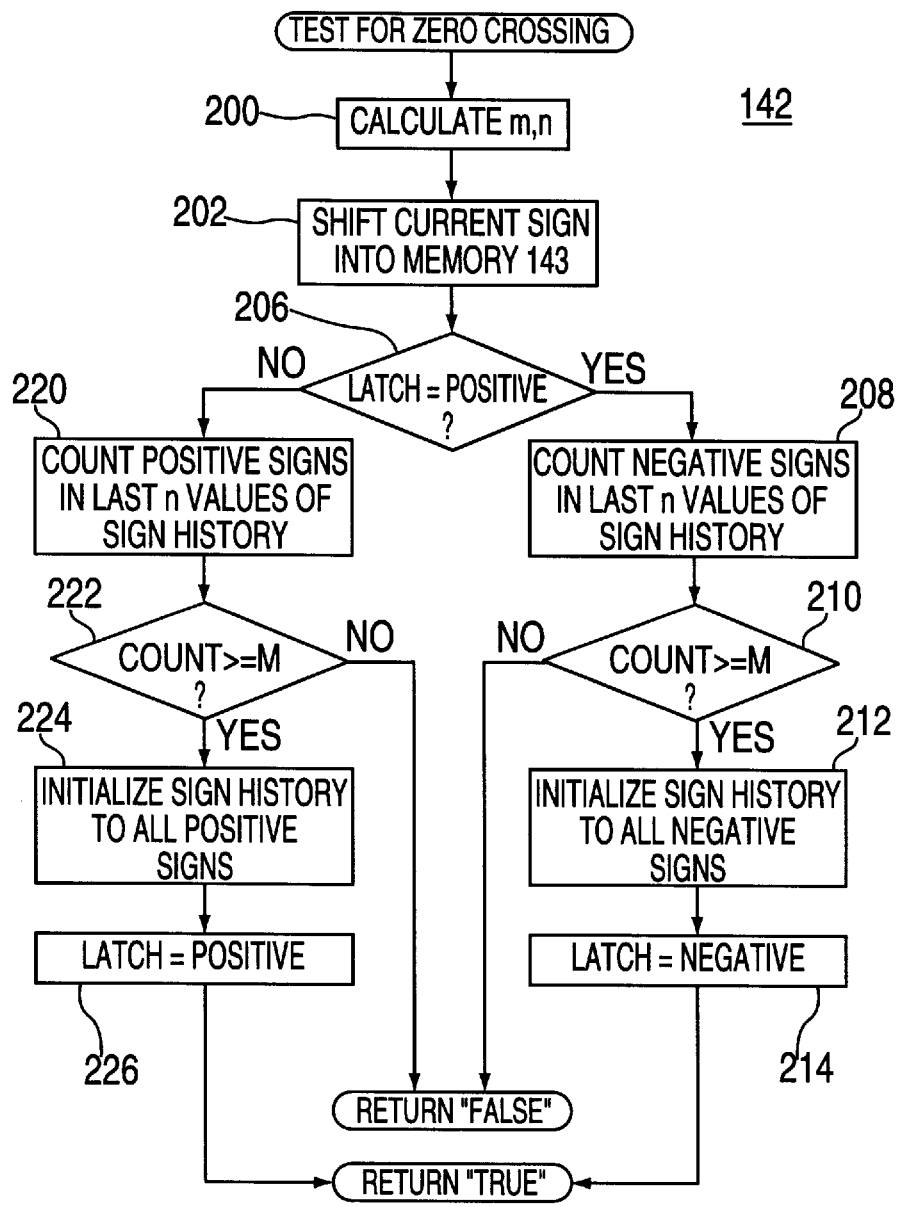
FIG. 7A shows a flow-chart for the circuit of FIG. 7 for determining a zero crossing.

The operation of the zero crossing detector 142 is shown in FIG. 7A and is now described.

Assume that at a particular instance in time t=0, a sample is converted by A/D converter 140. This sample has a sign $S_j$ which is either positive or negative and the zero crossing detector 142 must determine whether this sample corresponds to, or indicates, a zero crossing. This function is accomplished as follows. In step 200, the parameters m and n are calculated from the last N samples (whose sign $S_i$ has been stored in memory 143) using the formulas:

m=max(2,min(10,ceil(psi/dt)));

n=floor(1.5*m)

where psi/dt=the ratio of the paced or sensed interval to the sampling interval. A typical sampling interval is about 47 msecs.

The operation 'ceil' refers to rounding up to the nearest integer.

The operation 'floor' refers to rounding down to the nearest integer.

In step 202 the sign $S_j$ of latest sample is stored in memory 144 and the value of the oldest sample $S_{j-n}$ is discarded.

In step 206 a test is performed to check if the last zero-crossing referred to positive or negative crossing was positive. If the last crossing (indicated by a latch) was positive then in step 206 the number of negative sample values in the memory 144 from the least n samples is counted. In step 210, the count is compared to m. If count>m then in step 212 all the values in the polarity memory 144 are changed to negative.

In steps 220–226 a similar process is followed for a negative latch value.

If in steps 210 and 222 count<m, then signal $S_j$ does not indicate a zero crossing. Otherwise, at the end of steps 214 or 226, a zero crossing is indicated by circuit 142.

The zero crossing signal is sent to the compute circuit 144 (FIG. 7). The magnitude of the ti sample is also fed to the compute circuit 144 by A/D converter 140.

The magnitude calculation circuit 146 sums and stores the magnitude values (as shown in detail in FIG. 8A) for further processing in the compute circuit 148. The compute circuit 148 calculates an instantaneous minute volume (mv), tidal volume (tv) and respiration rate (rr) parameter every 1.5 seconds as shown in FIG. 8B. At least one full breath is included in each calculation to reduce the variability of the results. The various intermediate variables discussed below remain unchanged from one calculation to the next.

Figure 8A:
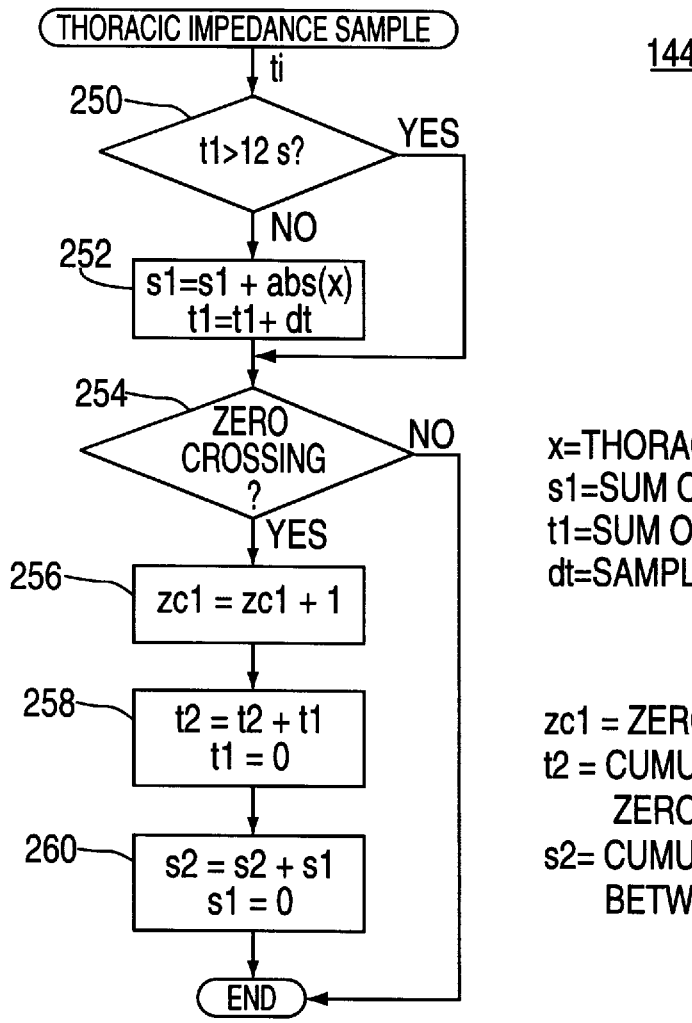
FIGS. 8A and 8B show flow charts for determining a first delta minute volume.
Figure 8B:
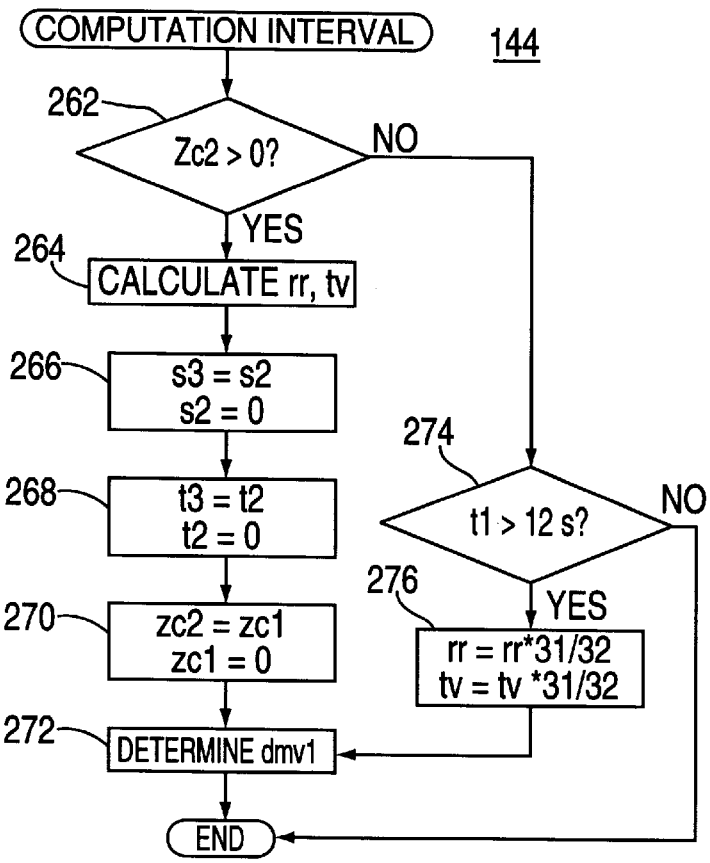

Referring first to the flow chart of FIG. 8A, first, in step 250, variable t1 is tested to see if it is longer than 12 seconds. This variable t1 is in effect a timer. If t1 is longer than 12 seconds, then a jump is made to step 254. Otherwise, in step 252 the variable s1 is incremented by the magnitude of the latest sample. The variable T1 is also incremented by the sampling interval dt. (As mentioned above the sampling interval dt is about 47 msec).

In step 254 a check is performed to determine whether the zero crossing detector 142 has identified the present sample as a zero crossing by circuit 142. If 'yes' then in step 256, a zero crossing counter zc1 is incremented by one, in step 258 a cumulative timer between t2 is incremented with t1 and t1 is reset to zero. In step 260 a cumulative sum s2 is incremented with s1 and the variable s1 is reset to zero. What is accomplished in FIG. 8A in effect is to perform an integration on the thoracic impedance ti. More specifically, the absolute value or magnitude of ti is integrated between the zero crossings. At each zero crossing the zero crossing counter zc1 is incremented and the cumulative time t2 and thoracic impedance values s2 are updated. The impedance values obtained during more than half of a breathing cycle are accumulated only at high respiration rates. If no zero crossings are detected for 12 seconds, the integration is interrupted (step 250) to insure that the intermediate integration variables do not overflow.

Having calculated the various intermediate variables, the calculate circuit 144 now calculates the output variables as follows (see FIG. 8B). In step 262 zc2 which is set to the old value of zc1 (i.e., prior to the performance of steps 250–260) is checked. If this variable is not zero, then in step 264 the variables rr and tv are calculated using the formulas:

$$rr=30*(zc1+zc2)/(t2+t3); \text{ and}$$

$$tv=gain*(s2+s3)/(t2+t3).$$

Where s2 is the sum of the absolute values of ti between zero crossings as determined in FIG. 8A, s3 is the previous value of s2;

t2 is the time between zero crossings as determined in FIG. 8A, t3 is the previous time;

The gain is a variable determined by circuit 110 as described below.

Next, in step 266 s3 is set to s2 and s2 is reset to zero. In step 268 t3 is set to t2 and t2 is set to zero. In step 270 zc2 is set to zc1 and zc1 is set to zero.

In step 272 a first delta minute volume parameter dmv1 is determined using the formula:

$$dmv1=tv*rr-\text{baseline}$$

where the baseline parameter is also determined by the circuit 106 as described below.

If in step 262 it is determined that zc2 is zero (i.e., no zc2 parameter has been determined in the previous calculation) in step 274 a check is performed to see if a period of 12 seconds has passed without a zero crossing being detected. If 'yes' then in step 276 the parameters rr and tv are reduced by a small fraction and the process continues.

In this manner, the parameters rr, tv and dmv1 are updated every 1.5 seconds if a corresponding zero crossing is detected. If no zero crossings are detected for up to 12 seconds, the values of these parameters are left unchanged. After 12 seconds without zero crossings, the values are gradually reduced toward the baseline parameter, to prevent inappropriate high rate pacing.

The procedure described above allows the pacemaker to measure respiration rate accurately, but tidal volume can be only approximated since the ratio of peak thoracic impedance to tidal volume varies from patient to patient. The gain parameter is chosen by circuit 106 so that an increase in the minute ventilation is related to the heart rate increase in a healthy patient. The following relationships approximate the relationships between heart rate hr (in BPM), tidal volume tv(in liters), and delta minute ventilation dmv (in liters per minute), based on patients having average heights and weights:

dmv=(hr-min_hr)/1.5 and tv=dmv/rr where min-hr is the heart rate at rest and rr is the respiration rate in breaths per minute.

Getting back to FIG. 7, after the parameters rr, tv and dmv1 the computed delta minute ventilation dmv1 is passed through the low-pass filter 150 to smooth the results. Preferably the filter 148 is a single pole low-pass filter, which has been found to model physiological response more closely than more complex filters. The filter is implemented preferably digitally, for example by using the equations given below. In a fixed-point arithmetic implementation an accumulator (incorporated in filter 150, not shown) must have more bits of precision than the delta minute ventilation values. The accumulator range is limited to prevent the filter from exhibiting delayed response following very high or very low input values.

a=a+(dmv1−a)*(w*dt/tc).
if (a>max_dmv)a=max_dmv
if (a<0)a=0
where:
dmv=a
dmv1=input (unfiltered delta minute ventilation from the circuit 148)
dmv=output (filtered delta minute ventilation)
a=the sum in the filter accumulator
w=sample weight
dt=time interval between iterations, typically 1.5 seconds
tc=time constant, typically 12 seconds
max_dmv=the value of MV which will map to max_hr (discussed more fully below).

Optionally, the parameters rr and tr are provided to filter 148 for performing an additional cross check function, wherein these two parameters are compared to generate a confidence level regarding the dmv determination. This feature is not part of the present invention and is described in more detail in application Ser. No. 08/848,968 filed May 2, 1997 and entitled RATE RESPONSIVE PACEMAKER WITH NOISE REJECTION MINUTE VOLUME DETERMINATION.

The output then of filter 148 is the delta minute volume parameter dmv in FIG. 5. Next, this parameter dmv must be converted into a metabolic indicated rate (MIR) parameter. Schemes for performing this function are well known in the art. One such scheme is disclosed in copending application Ser. No. 08/641,223 filed Apr. 30, 1996, and its continuation, application Ser. No. 08/823,077 filed Mar. 24, 1997 entitled RATE RESPONSIVE PACEMAKER WITH AUTOMATIC RATE RESPONSE FACTOR SELECTION incorporated herein by reference. As disclosed in this reference, a curvilinear mapping between minute ventilation and MIR is preferable because it can be modeled after physiological data on a wide range of normal subjects.

Figure 9:
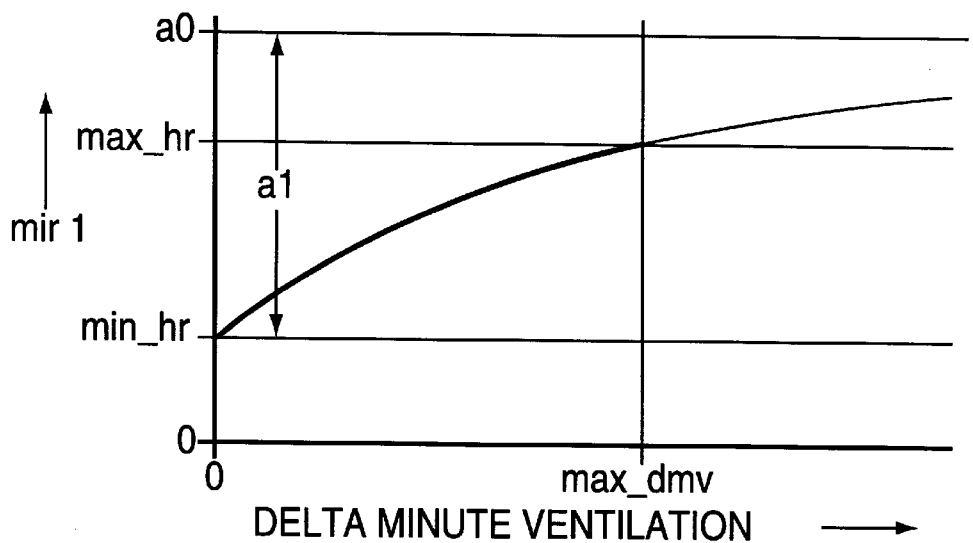
FIG. 9 shows an exponential mapping function mapping dmv in to MIR.

More particularly, it has been found that an excellent fit can be generated if an exponential mapping function is used. One such function is shown in FIG. 9. To save computational time, the exponential function may be performed by an interpolated table look-up function. The logarithmic function used to compute max_dmv is evaluated only by the programmer, at the time min_hr or max_hr is changed. The rate response factor (RRF) is defined so that one unit change in RRF relates to a 10% change in the peak value minute ventilation signal. It may be computed and displayed by the programmer, or may be entered by the user and used to initialize mv_gain.

The mapping function of FIG. 9 is defined by the following:

MIR1=a0−a1*exp(−dmv/a2)
max_dmv=a2*ln(a1/(a0−max_hr)) (used by low-pass filter 148)
a0=the upper heart rate asymptote, typically about 230 ppm
a1=a0−min_hr (a1 determines min_hr)
a2=max_dmv/ln(a1/a0−max_hr) (a2 determines max_hr)
dmv=filtered delta minute ventilation from delta mv generator 102
max_dmv=the maximum value of dmv which is mapped to max_hr
max_hr=the programmed maximum value of paced heart rate
RRF=rrf_const+ln(mv_gain/max_dmv)/ln(1.1)
mv_gain=max_dmv*1.1(RRF−rrf_const)
rrf_const is chosen to establish the nominal RRF value.

As indicated in FIG. 5, the parameter MIR1 is also fed to a gain and baseline calculating circuit 106. The gain and baseline circuit 106 is best implemented by fuzzy logic digital circuitry illustrated in FIGS. 10 and 11. The graph of FIG. 11 illustrates a typical cumulative percentile curve for subjects in the same age and fitness class. The target heart rates (thr0, thr1) and the cumulative percentiles (p0, p1) are chosen to fall on the portion of the curve 300 which is steepest and most repeatable for most patients. Two additional curves have been drawn to illustrate the effect of underpacing (pacing at too low a rate) (302) or overpacing (pacing at too high a rate) (304). The effects of the fuzzy logic rule base is to adjust the gain and baseline over time to approximate the standard curve. Target heart rate thr2 and cumulative percentile p2 are used as a cross-check to prevent overpacing in active patients who occasionally reach peak exercise levels.

Figure 10:
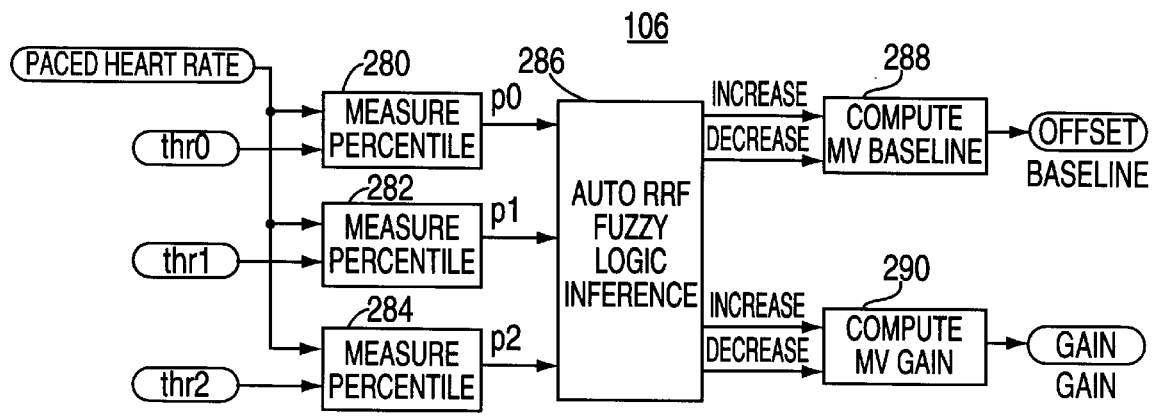
FIG. 10 shows a block diagram for circuit 110 in FIG. 5 for obtaining the MV gain and baseline.
Figure 11:
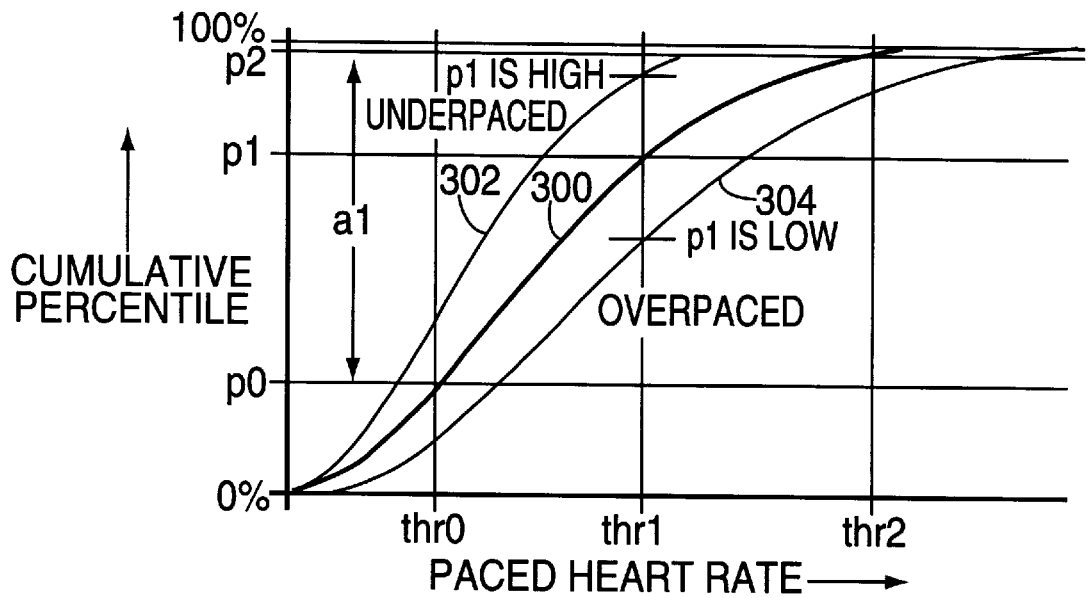
FIG. 11 shows graphs for cumulative percentiles used by the fuzzy logic circuit of FIG. 10.

Referring now to FIG. 10, target heart rate (thr0) is the programmed minimum paced heart rate, and represents the heart rate during sleep. The percentile (p0) is the percentage of time that the paced heart rate is less than the target heart rate. Every 1.5 seconds an accumulator 280 is incremented if the paced heart rate MIR2 is less than the target heart rate. Each 90 minutes the percentile value is computed and is transferred to a buffer containing the last 24 hours of data. The average percentile over the full contents of the buffer is computed and the accumulator is reset to zero.

Target heart rate (thr1) represents the heart rate during light exercise. Its value is chosen based on statistical data for patients. The percentile (p1) is computed in the same way as (p0). Target heart rate (thr2) is the programmed maximum paced heart rate, and represents the heart rate during peak exercise. The percentile (p2) is computed in the same way as (p0).

After these three parameters p0, p1, p2 are computed, a fuzzy logic inference circuit 286 is used to determine whether the baseline and the mv gain should be incremented or decremented.

Figure 12A:
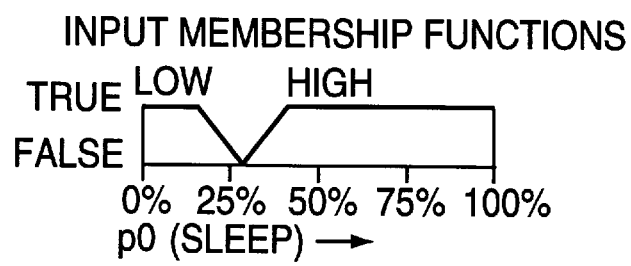
FIGS. 12A, B and C show the input membership function for obtaining the auto RRF fuzzy logic circuit 286 of FIG. 10.
Figure 12B:
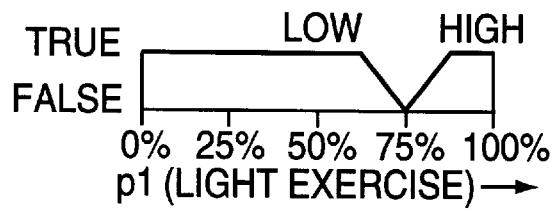
Figure 12C:
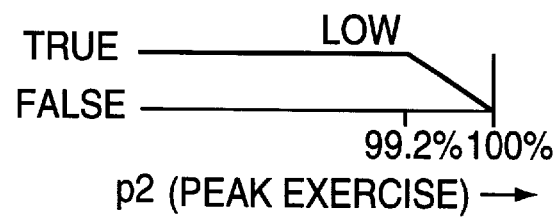

The fuzzy logic input membership functions for p0, p1 and p2 are shown in FIGS. 12A, 12B and 12C respectively. The circuit 286 makes use of the following inference rules:

R1: If p0 is LOW then increase the baseline.
R2: If p1 is HIGH then decrease the baseline.
R3: If p1 is LOW and p0 is not HIGH then decrease the gain.
R4: If p1 is HIGH and p0 is not LOW and p2 is not LOW then increase the gain.
R5: If p2 is LOW and p0 is not HIGH then decrease the gain.

The rational for these rules is that if p0, p1 or p2 is LOW then the patient is underpaced during the relevant activity, while a HIGH for the same parameters indicates that the patient is overpaced during the same exercise period.

Using these controls circuit 288 computes the MV baseline. This is performed every 90 minutes, based on the last 24 hours of data. To increase its value, a fixed fraction of max_mv, on the order of 1/32, is added to the accumulator. To decrease its value, the same fixed fraction of max_mv is subtracted from the accumulator. These adjustments are made additively in proportion to the truth value of each rule. The fractional value of 1/32 has been selected to allow a baseline adjustment of 50% of the full minute ventilation range over a period of one day. The rate of adjustment may be increased by decreasing the evaluation time intervals. Immediately after implant it may be desirable to allow more rapid adaptation; for instance, 15 minute intervals initially, increasing gradually to 90 minute intervals over a period of 2 days.

Similarly, the circuit 290 is used to calculate the mv gain parameter. More specifically, the gain is adjusted every 90 minutes, based on the last 24 hours of data. To increase its value, a fixed fraction of its current value, on the order of $1/128$, is added to an accumulator (not shown). To decrease its value, the same fixed fraction of its current value is subtracted from the accumulator. These adjustments are made additively in proportion to the truth value of each rule. The fractional value of $1/128$ has been selected to allow an effective time constant of eight days. The rate of adjustment may be increased by decreasing the evaluation time intervals. Immediately after implant it may be desirable to allow more rapid adaptation; for instance, 15 minute intervals initially, increasing gradually to 90 minute intervals over a period of eight days.

The two parameter mv gain and baseline are provided to the delta mv generator 102 (FIGS. 5, 7).

Getting back to FIG. 5, the parameter MIR1 is then used to generate a metabolic indicated rate interval (MRI) by calculator 108. The paced pulse interval is inversely related to the paced heart rate as indicated by the following equation.

ppi=60000/phr ppi=paced pulse interval, milliseconds phr=paced heart rate, pulses per second Other time intervals of the pacing cycle are computed by the state machine 53C (FIG. 4) using the paced pulse interval and/or the heart rate.

An alternate embodiment of computing minute ventilation for the calculator 102 is now presented. This method is based on averaging the absolute value of the derivative of the thoracic impedance signal and, unlike the implementation shown in FIG. 7, it does not require the use of a zero-crossing detector or any measurement of respiration rate.

Briefly, any method of computing minute ventilation involves a compromise between rapidity of response and rejection of artifacts or noise. All methods include some type of low-pass filter. If the cutoff frequency of the low-pass filter is increased, the response time is faster and the sensitivity to artifacts and noise is greater. The method presented herein is computationally simpler than method and apparatus shown in FIG. 7, and could be implemented entirely in hardware if desired.

The parameter delta MV (dmv) represents the increase of minute ventilation above a baseline. The baseline is the level of minute ventilation at which the paced heart rate is equal to the programmed minimum (min_hr). In this embodiment, minute ventilation is computed by averaging the absolute value of the derivative of the thoracic impedance signal. A cross-check function is included to reduce the effect of motion artifact.

Figure 13:
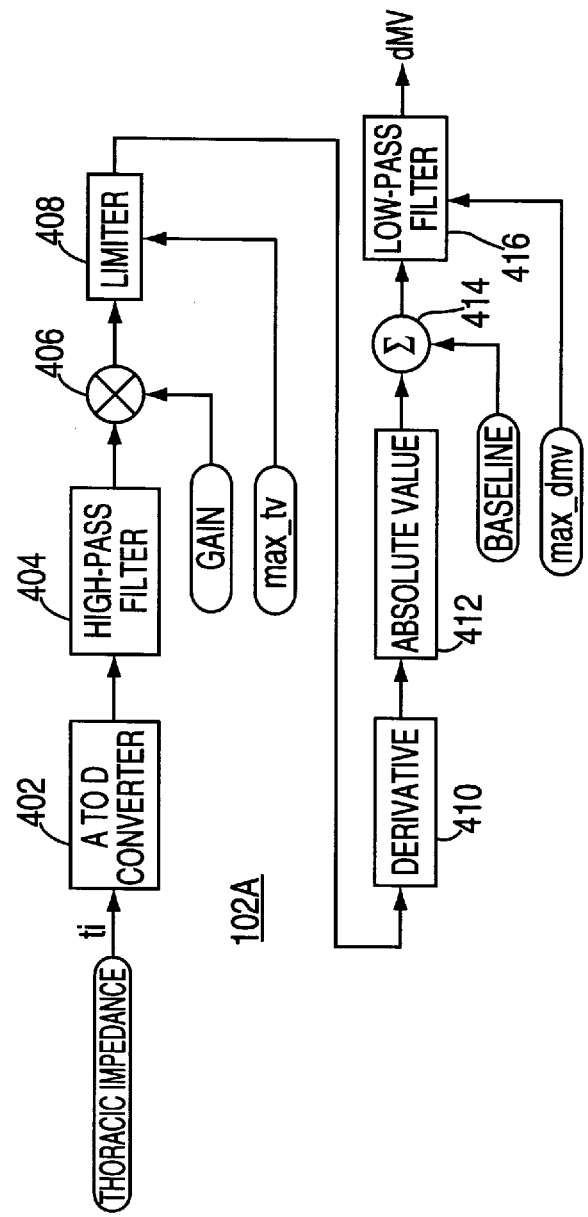
FIG. 13 shows the block diagram of an alternate embodiment for obtaining the minute ventilation.

Referring now to FIG. 13, circuit 102A for determining the dmv parameter includes several functional blocks such as an A/D converter 402, a high pass filter 404, a multiplier 406, a limiter 408, and a derivative calculator 410. Also included are an absolute value determinator 412, a summer 414, and a low pass filter 416.

Functional blocks or circuits 402–508 operate on, and generate an output for each sample of thoracic impedance ti. The remaining functional blocks or circuits 410–416 are operated at regular intervals such as every 1.5 seconds.

First the thoracic impedance parameter ti is fed to the A/D converter 402 which in response generates a digital representation of the instantaneous thoracic impedance, typically at the MV current-pulse rate.

The digital high-pass filter 404 is used to establish a constant baseline for the thoracic impedance measurement. This function may be deleted if the preceding circuits (used to generate ti) ensure a known constant baseline, or if the limiter 408 is not used. The filter 404 is implemented by using an accumulator (not shown) and performing the following equations. In a fixed-point arithmetic implementation the accumulator must have more bits of precision than the delta minute ventilation values.

a=a+(x−a)*(dt/tc)

y=x−a where x=input digital thoracic impedance, i.e. the input of the filter 404 y=output digital thoracic impedance, i.e., the output of the filter 404;

a=content of the accumulator dt=time interval between iterations, typically about 47 milliseconds tc=time constant, typically about 3 seconds (fc=0.05 Hz=3.2 bpm).

The output y of filter 404 is multiplied by multiplier 406 by the gain which is a function of the Rate Response Factor (RRF) and which can be determined as set forth above, and in FIG. 10. This operation scales the thoracic impedance into a corresponding tidal volume (tv) at a physiologically consistent value.

This unfiltered tidal volume signal tv is limited to a level max_tv, to reduce the effect of motion artifacts by limiter 408. The value of max_tv may be set to a constant, or may be determined for an individual patient by measuring the peak value at the output of the limiter 408 while the patient is asked to take several deep breaths. The following equations describe the operation of the limiter 408:

if(tv>max_tv) then 1out=max_tv;

else if (tv<−max_tv) then 1out=−max_tv;

else 1out=tv;

tv=input to the limiter 408

1out=output of limiter 408.

The derivative of tidal volume is computed by derivative calculator 410 at regular intervals such as every 1.5 seconds. Its magnitude is proportional to minute ventilation. The derivative calculator also includes an accumulator (not shown). The following equations describe the operation of the derivative calculator 410:

dout=(di−a)/dt a=di di=input tidal volume, i.e., the limited tidal volume from limiter 408;

dt=iteration interval a=the sum stored in the accumulator set to the previous value of di;

dout=output derivative of the tidal volume.

Next, the derivative of the tidal volume is fed to an absolute value determinator 412. The absolute value of the derivative is computed by this determinator 412 so that its magnitude may be averaged in the Low-Pass Filter 416.

Next, in summer 414, the baseline calculated in FIG. 5 is subtracted from the absolute value of the derivative of the tidal volume to obtain the delta minute volume.

Finally, the output of the summer 414 is fed to the low pass filter 416 so that the computed delta minute ventilation value is passed through a low-pass filter to smooth the results with the low-pass filter accumulator value being limited to fixed values of minute ventilation. The filter 416 is a single pole low-pass filter, which has been found to model physiological response more closely than more complex filters. The filter is implemented by the following equations. In a fixed-point arithmetic implementation the filter includes an accumulator which must have more bits of precision than the delta minute ventilation values. The accumulator value is limited to prevent the filter from exhibiting delayed response following very high or very low input values. The following equations describe the low-pass filter.

a=a+(dmv1−a)*(dt/tc)
if (a>max_dmv)a=max_dmv
else if (a<0)a=0
where dmv=a
   dmv1=input (unfiltered delta minute ventilation, i.e. the output of summer 414)
   dmv=output (filtered delta minute ventilation)
   a=accumulator
   dt=time interval between iterations, typically 1.5 seconds
   tc=time constant, typically 12 seconds
   max_dmv=the value of MV which will map to max_hr.

Figure 14A:
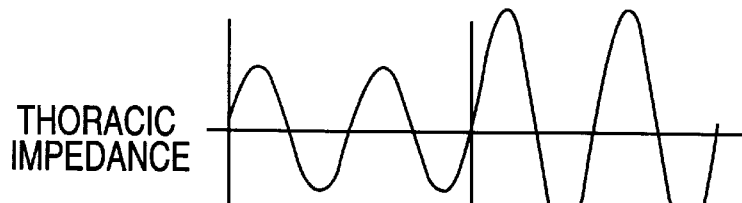
FIGS. 14A–B show various waveforms characteristic of the circuit of FIG. 13 for the thoracic impedance, limiter output and adaptive filter output, respectively.
Figure 14B:
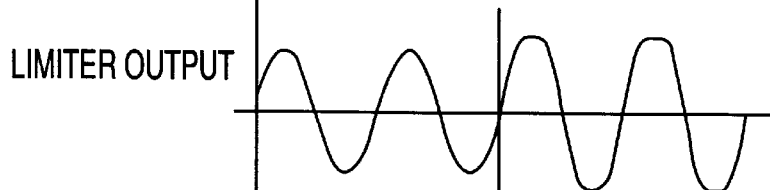
Figure 15A:
FIGS. 15A–D show characteristic waveshapes for the circuit of FIG. 13 for the differentiation input and output, absolute value and low pass filter.
Figure 15B:
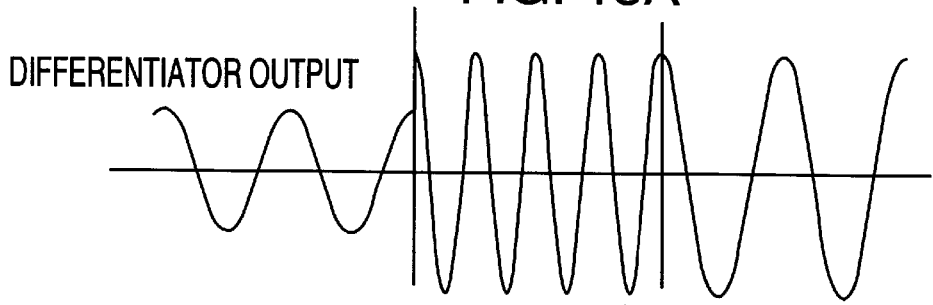
Figure 15C:
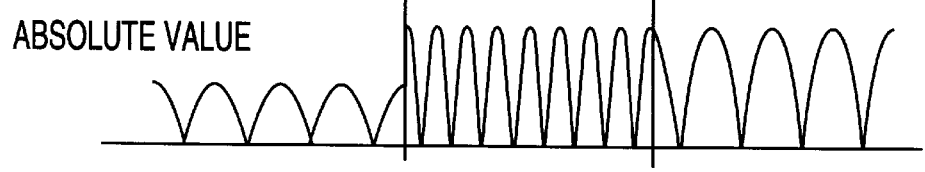
Figure 15D:
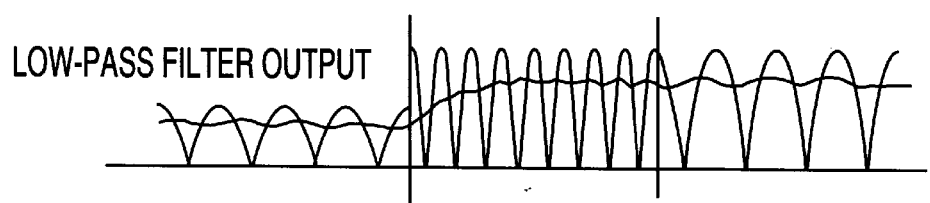

In this manner the parameter dmv is quickly and accurately determined by the circuitry of FIG. 13. FIGS. 14 and 15 show in analog form the intermediate signals generated therein. More specifically, FIG. 14A is the thoracic impedance, FIG. 14B shows the output of limiter 408. Similarly, FIG. 15A shows the input to derivative calculator 410 with a different waveform than FIG. 14B. FIG. 15B shows the output of derivative circuit 410, FIG. 15C shows the output of the absolute value determinator 412 and FIG. 15D shows the output of the low pass filter 416.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable pacemaker comprising:
   a. a cardiac sensor for sensing intrinsic activity in a patient's heart and generating a sensed signal;
   b. a pacing generator for generating pacing pulses in response to pacing commands;
   c. a metabolic demand generator for generating a metabolic demand signal indicative of the metabolic demand of the patient; and
   d. a controller for generating said commands corresponding to said sensed and metabolic demand signals; wherein said metabolic demand generator includes
      i. a metabolic sensor for generating a metabolic detected signal;
      ii. a metabolic detected signal processor for processing said metabolic detected signal in accordance with one of a paced and sensed heart rate, said signal processor including a derivative calculator for calculating a derivative of said metabolic detected signal; and
      iii. a signal generator for generating said demand signal based on said derivative and said sensed signal whereby said command signals have a fast response to exercise onset.

2. The pacemaker of claim 1 wherein said signal processor includes a zero crossing sensor for sensing zero crossings of said metabolic detected signal.

3. The pacemaker of claim 1 wherein said metabolic detected signal comprises a thoracic impedance.

4. The pacemaker of claim 1 wherein said metabolic detected signal comprises related to a tidal volume signal.

5. The pacemaker of claim 1 wherein said signal processor includes a breath sensor for sensing a respiration rate of the patient.

6. An implantable pacemaker comprising:
   a. a sensor for sensing intrinsic activity in a patient's heart and generating a sensed signal;
   b. a pacing generator for generating pacing pulses in response to pacing commands;
   c. a metabolic demand generator for generating a metabolic demand signal indicative of the metabolic demand of the patient; and
   d. a controller for generating said commands corresponding to said sensed and metabolic demand signals; wherein said metabolic demand generator includes
      i. a metabolic sensor for generating a metabolic detected signal, said metabolic detected signal having zero crossings; and
      ii. a metabolic detected signal processor for processing said metabolic detected signal into a metabolic demand signal, said processor being a fuzzy logic circuit and including a zero crossing detector for sensing said zero crossings in accordance with one of a paced and sensed heart rate.

7. The pacemaker of claim 6 wherein said zero crossing detector is constructed and arranged to adapt to said pacing and sensed heart rate.

8. An implantable pacemaker comprising:
   a. a sensor for sensing intrinsic activity in a patient's heart and generating a sensed signal;
   b. a pacing generator for generating pacing pulses in response to pacing commands;
   c. a metabolic demand generator for generating a metabolic demand signal indicative of the metabolic demand of the patient; and
   d. a controller for generating said commands corresponding to said sensed and metabolic demand signals; wherein said metabolic demand generator includes
      i. a metabolic sensor for generating a thoracic impedance signal;
      ii. a metabolic detected signal processor for processing said thoracic impedance signals characterized by thoracic impedance values, said processor including an accumulator for accumulating a plurality of values; and
      iii. a signal generator for generating said demand signal based on an output of said accumulator; wherein said signal generator generates said demand signal using a rate response function, said rate response function being an exponential curve.

9. The pacemaker of claim 8 wherein said processor further includes a moving average generator for generating a moving average of said values, said moving average being used to normalize said thoracic impedance signal with a baseline.

10. The pacemaker of claim 8 wherein said controller includes an interval detector for detecting an RR interval between intrinsic cardiac events and a tidal volume generator generating a tidal volume signal, said RR interval and said tidal volume signals being indicative of said thoracic impedance.

11. The pacemaker of claim 10 further comprising a noise sensing circuit, said RR interval and said tidal volume signals being adjusted to compensate for said noise signal.

* * * * *